(12) United States Patent
Mak et al.

(10) Patent No.: US 6,468,528 B1
(45) Date of Patent: Oct. 22, 2002

(54) MATERIALS AND METHODS TO INHIBIT HODGKIN AND REED STERNBERG CELL GROWTH

(75) Inventors: Tak W. Mak, Toronto (CA); Ursula Kapp, Freiburg (DE)

(73) Assignee: Amgen Canada Inc., Mississauga (CA)

( * ) Notice: Subject to any disclaimer, the term of this patent is extended or adjusted under 35 U.S.C. 154(b) by 0 days.

(21) Appl. No.: 09/496,155

(22) Filed: Feb. 1, 2000

Related U.S. Application Data

(60) Provisional application No. 60/118,018, filed on Feb. 1, 1999.

(51) Int. Cl.$^7$ .................... A61K 39/395; A61K 35/00; C07H 21/04; C07K 16/24; C07K 16/28

(52) U.S. Cl. .................. 424/130.1; 424/133.1; 424/141.1; 424/142.1; 424/143.1; 424/144.1; 424/145.1; 514/44; 530/387.1; 530/387.3; 530/388.15; 530/388.22; 530/388.23; 536/24.5

(58) Field of Search .................. 530/387.1, 387.3, 530/388.1, 388.15, 388.22, 388.23; 424/130.1, 133.1, 141.1, 142.1, 143.1, 144.1, 145.1; 514/44; 536/24.5

(56) References Cited

U.S. PATENT DOCUMENTS 6,086,874 A * 7/2000 Yoshida et al.
6,214,559 B1 * 4/2001 Collins et al.

FOREIGN PATENT DOCUMENTS

WO     WO 93/11236     6/1993

OTHER PUBLICATIONS

Newcome et al, "Interleukin–4 is an autocrine growth factor secreted by the L428 Reed Sternberg cell", Blood, 1992, vol. 79, pp. 191–197.*

Zurawski et al, "Receptors for interleukin–13 and interleukin–4 are complex and share a novel component that functions in signal transduction", EMBO, 1993, vol. 12, pp. 2663–2670.*

Bramlage, et al., "Designing ribozymes for the inhibition of gene expression," *Trends in Biotech* 16:434–438 (1998).

Cane, "Harnessing the Biosynthetic Code: Combinations, Permutations, and Mutations," *Science* 282:63–68 (1998).

Cossman, et al., "Reed–Sternberg Cell: Survival in a Hostile Sea," *Lab. Invest.* 78:229–235 (1998).

Del Prete, et al., "CD30–mediated Signalilng Promotes the Development of Human T Helper Type 2–like Cells," *J. Exp. Med.* 182:1655–1661 (1995).

Doucet, et al., "Interleukin (IL) 4 and IL–13 Act on Human Lung Fibroblasts," *J. Clin Invest* 101:2129–2139 (1998).

Drexler, "Recent Results on the Biology of Hodgkin and Reed–Sternberg Cells. I. Biopsy Material," *Leukemia and Lymphoma* 8:283–313 (1992).

Drexler, "Recent Results on the Biology of Hodgkin and Reed–Sternberg Cells," *Leukemia and Lymphoma* 9:1–25 (1993).

Emson, et al. "Interleukin (IL)–4–independent Induction of Immunoglobulin (Ig)E, and Perturbation of T Cell Development in Transgenic Mice Expressing IL–13," *J. Exp. Med.* 188:299–404 (1998).

Fonatsch, et al., "Assignment of the Human CD30 (Ki–1) Gene to 1p36," *Genomics* 14:825–826 (1992).

Gibson, et al., "Ribozymes," *Mol. Biotech.* 7:125–137 (1997).

Harlow, et al., *Antibodies A Laboratory Manual* Chapter 6 (1988).

Hui, et al., "A mouse model of Greig cephalo–polysyndactyly syndrome: the extra–toes$^J$ mutation contains an intragenic deletion of the Gli3 gene," *Nat. Genet.* 3:241–246 (1993).

Ikushim, et al., "Pivotal role for the NFIL3/E4BP4 transcription factor in interleukin 3–mediated survival of pro–B lymphocytes," *Proc. Natl. Acad. Sci. USA* 94:2609–2614 (1997).

Kadin, "Pathology of Hodgkin's disease," *Current Opinion in Oncology* 6:456–463 (1994).

Kanzler, et al., "Hodgkin and Reed–Sternberg Cells in Hodgkin's Disease Represent the Outgrowth of a Dominant Tumor Clone Derived from (Crippled) Germinal Center B Cells," *J. Exp Med.* 184:1495–1505 (1996).

Küppers, et al., "The Origin of Hodgkin and Reed/Sternberg Cells in Hodgkin's Disease," *Annu Rev Immunol* 16:471–491 (1998).

Larsson, et al., "The Human NOTCH1, 2, and 3 Genes Are Located at Chromosome Positions 9q34, 1p13–p11, and 19013.2–p13.1 in Regions of Neoplasia–Associated Translocation," *Genomics* 24:253–258 (1994).

Lavrovsky, et al., "Therapeutic Potential and Mechanism of Action of Oligonucleotides and Ribozymes," *Biochem. Mol. Med.* 62:11–22 (1997).

Lin, et al., "The Role of Shared Receptor Motifs and Common Stat Proteins in the Generation of Cytokine Pleiotropy and Redundancy by IL–2, IL–4, IL–7, IL–13, and IL–15," *Immunity* 2:331–339 (1995).

McKenzie, et al., "Impaired Development of Th2 Cells in IL–13 Deficient Mice," *Immunity* 9:423–432 (1998).

Minty, et al., "Interleukin–13 is a new human lymphokine regulating inflammatory and immune responses," *Nature* 362:248–250 (1993).

(List continued on next page.)

Primary Examiner—Anthony C. Caputa
Assistant Examiner—Karen A. Canella
(74) *Attorney, Agent, or Firm*—Marshall, Gerstein & Borun

(57) ABSTRACT

Materials and methods are disclosed for modulating proliferation of cell types associated with Hodgkin's disease through inhibition of IL-13 and components in IL-13 associated signal transduction pathways. Methods to identify inhibitors, compositions comprising the inhibitors, and methods using the inhibitors to treat Hodgkin's disease are also disclosed.

17 Claims, No Drawings

OTHER PUBLICATIONS

Myers, "Will Combinatorial Chemistry deliver real medicines?" *Curr. Opion. Biotechnol.* 8:701–707 (1997).

Robey, "Notch in vertebrates," *Curr. Opin. Genet. Dev.* 7:551–557 (1997).

Samoszuk, et al. "Detection of Interleukin–5 Messenger RNA in Reed–Sternberg Cells of Hodgkin's Disease With Eosinophilia," *Blood* 75:13–16 (1990).

Samoszuk, et al., "IgE in Reed–Sternberg Cells of Hodgkin's Disease With Eosinophilia," *Blood* 79:1518–1522 (1992).

Schena, et al., "Quantitative Monitoring of Gene Expression Patterns with a Complementary DNA Microarray," *Science* 270:467–470 (1995).

Schena, et al., "Parallel human genome analysis: Microarray–based expression monitoring of 1000 genes," *Proc. Natl. Acad. Sci. USA* 93:10614–10619 (1996).

Shahinian, et al., "Differential T Cell Costimulatory Requirements in CD28–Deficient Mice," *Science* 261:609–612 (1993).

Shalon, et al., "A DNA Microarray System for Analyzing Complex DNA Samples Using Two–color Fluorescent Probe Hybridization," *Genome Res.* 6:639–645 (1996).

Thangavelu, et al., "Chromosomal Abnormalities in Hodgkin's Disease," *Hematol. Oncol. Clin. North Am* 3:221–236 (1984).

Thomas, et al., "IgE Levels in Hodgkin's Disease," *Ann Allergy* 37:416–419 (1976).

Zurawski, et al., "Interleukin 13, an interleukin 4–like cytokine that acts on monocytes and B cells, but not on T cells," *Immunology Today* 15:19–26 (1994).

\* cited by examiner

MATERIALS AND METHODS TO INHIBIT HODGKIN AND REED STERNBERG CELL GROWTH

This application claims benefit of Application Ser. No. 60/118,018 filed Feb. 01, 1999.

FIELD OF THE INVENTION

The present invention relates generally to materials and methods for inhibition of Hodgkin and Reed Sternberg cell proliferation.

BACKGROUND OF THE INVENTION

Hodgkin's disease (HD) is unique among human lymphomas in that the tumor cells, known as Hodgkin and Reed Sternberg (H/RS) cells, are exceedingly rare, generally representing 0.1–1% of the total cell population within lymphoma tissue [Drexler, *Leukemia and Lymphoma* 8:283–313 (1992); Drexler, *Leukemia and Lymphoma* 9:1–25 (1993); Kadin, *Current Opinion in Oncology* 6:456:463 (1994); Cossman, et al., *Lab. Invest* 78:229–235 (1998)]. As a result, investigation of HRS cells has been impeded by their low frequency. PCR-based assays of DNA from single H/RS cells have revealed rearranged immunoglobulin genes and somatic mutations, suggesting that H/RS cells are clonal and may be derived from germinal center B cells [Kanzler, et al., *J Exp Med* 184:1495–505 (1996); Kyppers, et al., *Annu Rev Immunol* 16:471–93 (1998)]. The precise pathogenesis of HD, however, remains to be determined.

Previous observations suggest that the proliferation and survival of HD-derived cells depends on cytokine signaling. It is well established that the unique histology and eosinophilia of HD tissues, and secondary symptoms in the patient such as fever, weight loss, and night sweats, are induced by a pathological pattern of cytokine secretion [Drexler, *Leukemia and Lymphoma.* 8:283–313 (1992); Drexler, *Leukemia and Lymphoma* 9:1–25 (1993)]. For example, overexpression of IL-5 in H/RS cells has been previously demonstrated by in situ hybridization, but only in HD patients exhibiting eosinophilia [Samoszuk, et al., *Blood* 75:13–16 (1990); Samoszuk, *Blood* 79:1518–22 (1992)]. To date, no cytokine has been consistently reported as being overexpressed in HD-derived cell lines or in primary H/RS cells.

Evidence for a role for IL-13 in the etiology of HD is indirect. IgE is elevated in HD tissues and serum samples from HD patients [Samoszuk, *Blood* 79:1518–22 (1992); Thomas, et al., *Ann Allergy* 37:416–19 (1976)], and IL13 is known to promote Ig class switching to IgE. IL13-deficient mice exhibit lower basal levels of serum IgE [McKenzie, et al., *Immunity* 9:423432 (1998)]. Furthermore, studies of IL-4 deficient, IL-13 transgenic mice have demonstrated that IL-13 can promote class switching to IgE independently of IL-4 [Emson, et al., *J Exp. Med* 188:399404 (1998)], emphasizing that IL-4 and IL-13 have distinct roles in regulating B cell functions.

IL-13 is a T cell-derived cytokine with immunomodulatory and anti-inflammatory properties [Minty, et al., *Nature* 362:248–250 (1993)]. The biological effects of IL-13 on B cells, macrophages, and monocytes are very similar to those of IL-4, probably because the IL-4 and IL-13 receptors share a common a chain. In B cells, IL-13 promotes proliferation, differentiation, and Ig heavy chain class switching to IgE and IgG4 [Zurawski, et al., *Immunology Today* 15:19–26 (1994)]. Proliferation results from a signaling pathway in which the engagement of the IL-13 receptor activates JAK1, which in turn activates STAT6 [Lin, et al., *Immunity* 2:331–339 (1995)].

Other aspects of the HD phenotype may also be attributable to the effects of IL-13. A recent study of IL-13-deficient mice has shown that cultures of type 2 helper T (Th2) cells from these animals produce significantly reduced levels of IL-4, IL-5, and IL-10 compared to the wild type, suggesting an important role for IL-13 as a regulator of Th2 cell commitment [McKenzie, et al, *Immunity* 9:423–432 (1998)]. If IL-13 is also important for promoting the differentiation of Th2 cells in humans, it could explain why H/RS cells (which secrete IL-13) are surrounded by Th2 cells in HD biopsies. In addition, because fibroblasts express the IL-13 receptor and can be activated by IL-13 [Doucet, et al., *J Clin Invest* 101:2129–2139 (1998)], the secretion of IL-13 by H/RS cells may underlie the pathogenesis of the fibrosis observed in nodular sclerosis HD.

Thus, there exists a need in the art to identify specific growth factors that participate in the pathogenesis of HD. In particular, identification of cytokines that stimulate H/RS cell proliferation will facilitate development of methods for therapeutic invention, by way of (i) modulating expression of the cytokine(s), (ii) modulating biological activity of the cytokine(s), and (iii) modulating both expression and biological activity.

SUMMARY OF THE INVENTION

The present invention provides materials and methods for inhibiting proliferation of cell types associated with Hodgkin's disease. In particular, the invention contemplates inhibiting proliferation of Reed Sternberg cells found in individuals suffering from Hodgkin disease. Reed Sternberg cells associated with Hodgkin's disease are referred to herein as H/RS cells.

The invention comprehends various methods by which proliferation of H/RS cells can be modulated, preferably through mechanisms that modulate expression, secretion, stimulation, activation, and/or biological activity of IL-13 and/or its cognate IL-13 receptor, as well as components in signal transduction pathways associated with IL-13 and the IL-13 receptor. In one aspect, the invention provides methods for inhibiting IL-13 dependent proliferation of Hodgkin and Reed Sternberg (H/RS) cell types comprising the step of contacting the H/RS cells with a compound that inhibits biological activity of IL-13. In a preferred embodiment, methods are provided wherein the compound that inhibits IL-13 biological activity is an antibody. It is preferred that the antibody is a monoclonal-antibody that specifically recognizes and binds to IL-13, and most preferably, the monoclonal antibody is a human antibody, however, humanized antibodies and non-human antibodies are also comprehended by the invention.

Get a PCT Publication for Humanized Antibodies

The term "specifically recognizes or binds" as used herein indicates antibodies of the invention bind to only IL-3, IL-13 receptor, or naturally occurring variants thereof, despite any sequence similarity, homology, or identity conserved in other polypeptides.

In another aspect, the invention provides methods for inhibiting IL-13 dependent proliferation of Hodgkin and Reed Sternberg (H/RS) cell types comprising the step of contacting the H/RS cell types with a compound that inhibits biological activity of IL-13 receptors expressed on the H/RS cell types. In a preferred embodiment, methods are provided wherein the compound that inhibits IL-13 receptor biological activity is an antibody. It is preferred that the antibody is a monoclonal antibody that specifically recognizes and binds to the IL-13 receptor, and most preferably, the monoclonal antibody is a human antibody, however, humanized antibodies and non-human antibodies are also comprehended by the invention.

Alternatively, the invention provides methods for inhibiting IL-13 dependent proliferation of Hodgkin and Reed Sternberg (H/RS) cell types comprising the step of contacting the H/RS cells with a compound that inhibits expression of IL-13. In a preferred embodiment, methods of the invention are provided wherein the compound that inhibits IL-13 expression is an antisense polynucleotide that specifically recognizes a polynucleotide encoding IL-13. In another preferred embodiment, methods are provided wherein the compound that inhibits IL-13 expression is a ribozyme that binds to and acts specifically on polynucleotides encoding IL-13. The terms "act specifically on" and "specifically recognizes or binds" as used herein indicates that anti-sense and ribozymes of the invention bind to and act only on polynucleotides that encode IL-13, the IL-13 receptor, or naturally occurring variants thereof despite any sequence similarity, homology, or identity conserved in polynucleotides encoding other polypeptides.

Similarly, the invention also provides methods for inhibiting IL-13 dependent proliferation of Hodgkin and Reed Sternberg (H/RS) cell types comprising the step of contacting the H/RS cells with a compound that inhibits expression of IL-13 receptor. In a preferred embodiment, methods of the invention are provided wherein the compound that inhibits IL-13 receptor expression is an antisense polynucleotide that specifically recognizes a polynucleotide encoding the IL-13 receptor. In another preferred embodiment, methods are provided wherein the compound that inhibits IL-13 receptor expression is a ribozyme that binds to and acts specifically on polynucleotides encoding the IL-13 receptor.

The invention comprehends methods for identifying a compound that inhibits IL-13 dependent proliferation of Hodgkin and Reed Sternberg (HI/S) cell types comprising the steps of: a) measuring binding between IL-13 with IL-13 receptor in the presence and absence of a candidate inhibitor compound; and b) identifying the candidate compound as an inhibitor when binding between IL-13 and the IL-13 receptor is less in the presence of the candidate compound than in the absence of the candidate compound. The invention also provides methods for identifying a compound, or combination of compounds, that inhibits IL-13 dependent proliferation of Hodgkin and Reed Sternberg (H/RS) cell types comprising the steps of: a) contacting IL-13 with IL-13 receptor, b) measuring binding between IL-13 and the IL-13 receptor; c) repeating step (a) in the presence of a candidate inhibitor compound or compounds; d) repeating step (b) in the presence of the candidate compound or compounds; and e) identifying the candidate compound or compounds as an inhibitor when binding between IL-13 and the IL-13 receptor is less in the presence of the candidate compound than in the absence of the candidate compound. In a preferred embodiment of the method, IL-13 receptor is expressed on the cell surface of the H/RS cell types.

The invention also provide methods to identify a compound that inhibits IL-13 dependent proliferation of Hodgkin and Reed Sternberg (H/RS) cell types comprising the steps of: a) measuring IL-13 expression from growing H/RS cells in the presence and absence of a candidate inhibitor compound; and b) identifying the candidate compound as an inhibitor when lower levels of IL-13 expression are measured in the presence of the candidate compound than in an absence of the candidate compound. In one aspect, the invention provides methods to identify a compound or combination of compounds that inhibits IL-13 dependent proliferation of Hodgkin and Reed Sternberg (H/RS) cell types comprising the steps of: a) growing H/RS cell types; b) measuring IL-13 expression; c) incubating the cell with a candidate inhibitor compound or compounds; d) measuring IL-13 expression with the candidate compound or compounds; and e) identifying the candidate compound or compounds as an inhibitor when lower levels of IL-13 expression are measured with the candidate compound or compounds than in an absence of the candidate compound or compounds. In a preferred embodiment of the method, the candidate inhibitor compound is an anti-sense polynucleotide that specifically binds to a polynucleotide encoding IL-13.

In methods of the invention in which IL-13 or IL-13 receptor biological activity is inhibited, numerous modes of action for a candidate Inhibitor are contemplated. In one aspect, inhibitors are provided that bind and neutralize IL-13. Preferably, an inhibitor acting by this mechanism prevents interaction between IL-13 and the IL-13 receptor. The invention comprehends mechanisms by which the inhibitor binding interaction induces a conformational change in IL-13, and binding that results in stearic hindrance preventing receptor recognition. The invention further comprehends inhibitors of the IL-13 receptor biological activity, which like IL-13 inhibitors, can function in a variety of ways. In one aspect, the IL-13 receptor inhibitor binds and neutralizes IL-13 activity. Preferably, the inhibitor would prevent interaction of the receptor with IL-13, or may prevent interaction of the IL-13 receptor with some downstream component of an IL-13 metabolic pathway that is required for, or participates in, H/RS cell proliferation. For example, it is known that IL-13 receptor activates JAK 1 and the invention therefore embraces inhibitors that prevent this activation, directly or indirectly.

The invention further embraces methods to inhibit activity of or interaction between, components in IL-13 pathways downstream from the IL-13 receptor that are required for, or at least participate in, H/RS cell proliferation.

In identification of inhibitors, the invention provides various sources for candidate compounds. There are a number of different libraries used for the identification of small molecule modulators, including, (1) chemical libraries, (2) natural product libraries, and (3) combinatorial libraries comprised of random peptides, oligonucleotides or organic molecules. Chemical libraries consist of structural analogs of known compounds or compounds that are identified as "hits" or "leads" via natural product screening. Natural product libraries are collections of microorganisms, animals, plants, or marine organisms which are used to create mixtures for screening by: (1) fermentation and extraction of broths from soil, plant, or marine microorganisms or (2) extraction of plants or marine organisms. Natural product libraries include polyketides, non-ribosomal peptides, and variants (non-naturally occurring) thereof. For a review, see *Science* 282:63–68 (1998). Combinatorial libraries are composed of large numbers of peptides, oligonucleotides, or organic compounds as a mixture. They are relatively easy to prepare by traditional automated synthesis methods, PCR, cloning or proprietary synthetic methods. Of particular interest are peptide and oligonucleotide combinatorial libraries. Still other libraries of interest include peptide, protein, peptidomimetic, multiparallel synthetic collection, recombinatorial, and polypeptide libraries. For a review of combinatorial chemistry and libraries created therefrom, see Myers, *Curr. Opion. Biotechnol.* 8:701–707(1997). Identification of modulators ("hits") through use of the various libraries described herein permits modification of the candidate "hit" (or "lead") to optimize the capacity of the "hit" to modulate activity. Methods of the invention are particularly amenable to high throughput screening (HTS) assays wherein large numbers of candidate inhibitors can been screen simultaneously, preferably by automated mechanisms.

In another aspect, the invention provides antibodies that inhibit IL-13 or IL-13 receptor activity. The invention provides monoclonal and polygonal antibodies, single chain antibodies, chimeric antibodies, and CDR-grafted antibodies, including compounds which include CDR sequences which specifically recognize a polypeptide of the invention. In a preferred embodiment, the invention provides human antibodies that specifically recognize IL-13, IL-13 receptor, other components in IL-13 pathways that participate in H/RS cell proliferation, and naturally occurring variants thereof. Human antibodies are produced and identified according to methods described in WO93/11236, published Jun. 20, 1993, which is incorporated herein by reference in its entirety. The term "specifically recognize" indicates that the variable regions of the antibodies recognize and bind, for example IL-13 or IL-13 receptor polypeptides, exclusively (i.e., able to distinguish IL-13 the IL-13 receptor, or naturally occurring variants thereof, from closely related polypeptides despite sequence identity, homology, or similarity found in the structure of the polypeptides), but may also interact with other proteins (for example, *S. aureus* protein A or other antibodies in ELISA techniques) through interactions with sequences outside the variable region of the antibodies, and in particular, in the constant region of the molecule. Screening assays to determine binding specificity of an antibody of the invention are well known and routinely practiced in the art. For a comprehensive discussion of such assays, see Harlow et al. (eds), *Antibodies A Laboratory Manual;* Cold Spring Harbor Laboratory; Cold Spring Harbor, NY (1988), Chapter 6. Antibodies that recognize and bind fragments of; for example, IL-13 or IL 13 receptor polypeptides of the invention, are also contemplated, provided that the antibodies are first and foremost specific for intact (ie., "unfragmented") polypeptides. As with antibodies that are specific for full length IL-13 or IL-13 receptor polypeptides (or other polypeptides of the invention), antibodies that recognize IL-13 or IL-13 receptor fragments are those which can distinguish IL-1–13 or IL-13 receptor polypeptides from other polypeptides despite inherent sequence and structural identity, homology, or similarity.

As still another aspect, the invention provides antisense polynucleotides which inhibit translation of a polynucleotide encoding IL-13, IL-13 receptor, other components of an IL-13 pathway that participate in H/RS cell proliferation, and naturally occurring variants thereof. Full length and fragment anti-sense polynucleotides are provided. The worker of ordinary skill will appreciate that fragment antisense molecules of the invention include (i) those which specifically recognize and hybridize to, for example either IL-13 or IL-13 receptor, RNA (as determined by sequence comparison of DNA encoding IL-13 or the IL-13 receptor to DNA encoding other known molecules and identification of characteristic or signature sequences) as well as (ii) those which recognize and hybridize to RNA encoding variants of the, for example, IL-13 or IL-13 receptor family of proteins. Antisense polynucleotides that hybridize to RNA encoding related members of the IL-13 or IL-13 receptor families of proteins are also identifiable through sequence comparison to identify characteristic, or signature, sequences for either family of molecules.

The invention further contemplates methods to modulate IL-13,IL-13 receptor, other components of an IL-13 pathway that participate in H/RS cell proliferation, and naturally occurring variants thereof, expression through use of ribozymes. For a review, see Gibson and Shillitoe, *Mol. Biotech* 7:125–137 (1997). Ribozyme technology can be utilized to inhibit translation of, for example, IL-13 or IL-13 receptor mRNA in a sequence specific manner through (i) the hybridization of a complementary RNA to a target mRNA and (ii) cleavage of the hybridized mRNA through nuclease activity inherent to the complementary strand. Ribozymes can be identified by empirical methods, but more preferably are specifically designed based on accessible sites on the target mRNA (Bramlage, et al., *Trends in Biotech* 16:434–438 (1998). Delivery of ribozymes to target cells can be accomplished using either exogenous or endogenous delivery techniques well known and routinely practiced in the art. Exogenous delivery methods can include use of targeting liposomes or direct local injection. Endogenous methods include use of viral vectors and non-viral plasmids.

Ribozymes can specifically modulate expression of IL-13, IL-13 receptor, other components of an IL-13 pathway that participate in H/RS cell proliferation, and naturally occurring variants thereof when designed to be complementary to regions unique to a polynucleotide encoding either polypeptide. "Specifically modulate" therefore is intended to mean that ribozymes of the invention recognizes only a polynucleotide encoding, for example, either IL-13 or the IL-13 receptor. Similarly, ribozymes can be designed to modulate expression of all or some of the proteins closely related to either IL-13 or the IL-13 receptor. Ribozymes of this type are designed to recognize polynucleotide sequences conserved in all or some of the polynucleotides which encode the family of proteins.

The invention further embraces methods to modulate transcription of IL-13, IL-13 receptor, other components of an IL-13 pathway that participate in H/RS cell proliferation, and naturally occurring variants thereof, through use of oligonucleotide-directed triplet helix formation. For a review, see Lavrovsky, et al., *Biochem. Mol. Med* 62:11–22 (1997). Triplet helix formation is accomplished using sequence specific oligonucleotides which hybridize to double stranded DNA in the major groove as defined in the Watson-Crick model. Hybridization of a sequence specific oligonucleotide can thereafter modulate activity of DNA-binding proteins, including, for example, transcription factors and polymerases. Preferred target sequences for hybridization include promoter and enhancer regions to permit regulated transcription of IL-13, IL-13 receptor, other components of an IL-13 pathway that participate in H/RS cell proliferation, and naturally occurring variants thereof Oligonucleotides which are capable of triplet helix formation are also useful for site-specific covalent modification of target DNA sequences. Oligonucleotides useful for covalent modification are coupled to various DNA damaging agents as described in Lavrovsky, et al. [supra].

The invention further provides methods for treating Hodgkin's Disease comprising the steps of administering to an individual in need thereof a therapeutically effective amount of a compound that inhibits IL-13 biological activity. Similarly, the invention contemplates methods for treating Hodgkin's Disease comprising the steps of administering to an individual in need thereof a therapeutically effective amount of a compound that inhibits IL-13 expression. In a preferred method, the inhibitor is an antisense polynucleotide that specifically binds a polynucleotide encoding IL-13 or an antibody that specifically recognizes an IL-13 polypeptide.

The invention also comprehends methods for treating Hodgkin's Disease comprising the step of administering to an individual in need thereof a therapeutically effective amount of a compound that inhibits IL-13 receptor biological activity. In another sect, the invention provides methods for treating Hodgkin's Disease comprising the step of administering to an individual in need thereof a therapeutically effective amount of a compound that inhibits IL-13 receptor expression.

Inhibitors of the invention can be administered in combination with a pharmaceutically acceptable (i.e., sterile and non-toxic) liquid, semisolid, or solid diluents that serve as pharmacuetical vehicles, excipients, or media. Any diluent known in the art may be used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of theobroma.

The inhibitor compositions can be packaged in forms convenient for delivery. The compositions can be enclosed within a capsule, sachet, cachet, gelatin, paper, or other container. These delivery forms are preferred when compatible with entry of the composition into the recipient organism and, particularly, when the composition is being delivered in unit dose form. The dosage units can be packaged, e.g., in tablets, capsules, suppositories or cachets.

The inhibitor compositions may be introduced into the subject by any conventional method including, e.g., by intravenous, intradermal, intramuscular, intramammary, intraperitoneal, or subcutaneous injection; by oral, sublingual, nasal, anal, vaginal, or transdermal delivery; or by surgical implantation, e.g., embedded under the splenic capsule or in the cornea. The treatment may consist of a single dose or a plurality of doses over a period of time. Optimal dosages may be readily determined by routine methods.

In another aspect, the invention contemplates use of an inhibitor of IL-13 expression in the production of a medicament for treatment of IL-13 dependent Hodgkin and Reed Sternberg cell proliferation. As another aspect, use of an inhibitor of IL-13 receptor biological activity in the production of a medicament for treatment of IL-13 dependent Hodgkin and Reed Sternberg cell proliferation is also provided. The invention also embraces use of an inhibitor of IL-13 receptor expression in the production of a medicament for treatment of IL-13 dependent Hodgkin and Reed Sternberg cell proliferation. In still another aspect, the invention comprehends use of an inhibitor of IL-13 biological activity in the production of a medicament for treatment of IL-13 dependent Hodgkin and Reed Sternberg cell proliferation.

While the invention is exemplified with respect to expression and biological activity of IL-13 and its cognate receptor, the invention also comprehends materials and methods to modulate expression and biological activity of other compounds (and their receptors where applicable) demonstrated herein to have high expression levels in H/RS cells, including for example, IL-5, ornithine decarboxylase (ODC), ICAM-3, urokinase (UPA), IgE Fc receptor II, insulin-like growth factor (IGF) II, NF-IL-3AE4BP4, Notch2, GM-CSF, interferon regulatory factors (IRF) 1, 5 and 6, nitric oxide synthase (NOS) 3, and the T cell receptor delta chain. The invention also comprehends materials and methods to modulate expression and biological activity of compounds in IL-13 pathways that participate, directly or indirectly, in H/RS cell proliferation.

DETAILED DESCRIPTION OF THE INVENTION

The present invention is exemplified in the following examples. Example 1 describes identification of genes differentially expressed in H/RS cells. Example 2 describes Northern analysis and ELISA to confirm results observed in Example 1. Example 3 provides even more confirmatory evidence of differential gene expression using in situ hybridization. Example 4 demonstrates that neutralization of IL-13 activity modulates H/RS cell proliferation.

EXAMPLE 1

Gene Expression in HD Cells

In a first series of experiments, assays were carried out to compare overall gene expression in a HD-derived cell type compared to a normal cell line in an attempt to identify genes that are over-expressed in the HD cells. Microarray analysis has recently been developed [Schena, et al., *Science* 270:467470 (1995); Schena, et al. *Proc Natl Acad Sci USA* 93:10614–10619, (1996); Shalon, et al., *Genome Res* 6:639–645 (1996)] as a very efficient means of studying the differential expression of many genes simultaneously. Gene expression in two different samples is compared using competitive hybridization of two probes labeled with different fluorescent dyes.

In the first experiments, cDNA segments from genes relevant to inflammation and neoplasia were used to examine gene expression patterns in HD-derived cell lines. Microarray expression patterns in the aneuploid, clonal cell lines L428 and KMH2[Drexler, *Leukemia and Lymphoma* 9:1–25 (19.93)], which were cultured from Hodgkin tissues and are regarded as HD cell lines, were compared with microarray expression patterns in control LCL-GK cells, an Epstein Barr virus (EBV) infected lymphoblastoid B cell line from a healthy individual. Additional control cells included EBV negative, non-Hodgkin lymphoma (NHL) cell lines Ly4, Ly7, and Ly13.2. The cell lines were grown in IMDM medium supplemented with penicillin, streptomycin, and 10% fetal calf serum.

From each cell type, poly(A)$^+$ mRNA was prepared from total RNA using Oligotex-dT resin (QIAGEN, Chatsworth, Ga.) according to the manufacturer's suggested protocol. Each mRNA sample was converted into fluorescein-labeled CDNA probes using the microarray (GEM) probe labeling kit (Synteni, Palo Alto, Calif., USA), also according to manufacturer's suggested protocol. The microarray used in these experiments contained 950 human genes involved in inflammation and neoplasia (Synteni, Palo Alto, Calif., USA). Two microarrays were independently probed with 200 ng of a 1:1 mixture of fluorescein-labeled cDNA from HD-derived L428 cells and control LCL-GK cells on microarray 1 (M1) or from HD-derived KMH2 cells and LCL-GK cells on microarray 2 (M2). Known concentrations of mRNA synthesized from inter-ORF regions from *S. cerevisiae* were used as quantitation standards. The hybridization was performed as previously described [Schena, et al., 1995. *Science* 270:467470 (1995)].

Of the 950 genes displayed on the microchip, those showing greater than three-fold difference in expression in both HD-derived cell lines were: IL-13, IL-5, ornithine decarboxylase (ODC), ICAM-3, urokinase (UPA), IgE Fc receptor II, insulin-like growth factor (IGF) II, NF-IL-3/ E4BP4, Notch2, GM-CSF, interferon regulatory factors (IRF) 1, 5 and 6, nitric oxide synthase (NOS) 3, and the T cell receptor delta chain. IL-13 expression in HD-derived L428 and KMH2 cells was increased over that in control LCL-GK cells 26.7- and 17.1-fold, respectively, while IL-5 expression was increased by 14.2- and 18.5-fold, respectively. In addition, mRNA for the IL-13 receptor was found to be expressed in both HD-derived cell lines tested.

These results clearly demonstrate that HD-derived cell lines and H/RS tumor cells express elevated levels of IL-13. Because IL-13 is known to promote IgE class switching, the elevation of IgE in H/RS cells and in the serum of HD patients could be explained if IL-13 secreted by H/RS cells affects both the H/RS cells themselves and bystander B cells.

As discussed above, the microarray hybridization showed that the expression of NF-IL-3 and Notch2 was upregulated by more than 3-fold in NBL-derived cell lines. The basic leucine zipper (b-ZIP) transcription factor NF-IL-3 acts downstream of IL-13 and has been shown to prevent apoptosis after forced expression in an IL-13-dependent pro-B cell line [Ikushima, et al., *Proc Natl Acad Sci USA* 94:2609–2614 (1997)]. The relevance of NF-IL-3 in HD is unknown.

Notch 2 is a transmembrane receptor that has been shown to be involved in cell fate decisions [Robey, *Curr Opin Genet Dev* 7:551–7.(1997)]. The human Notch2 gene has been mapped to chromosome 1 at position 1p13–p11, which is a region of translocations associated with neoplasia [Larsson, et al., *Genomics* 24:253–58 (1994)].

Chromosome 1 has also been linked to the HD phenotype, since structural rearrangements of chromosome 1 are frequently observed in HD [Thangavelu, et al., *Hematol Oncol Clin North Am* 3:221–36 (1984)].

Interestingly, the gene for CD30, which was first identified in the HD-derived cell line L428 [Schwab, et al., *Nature* 299:65–67 (1982)] and is considered a marker for the disease, is also located on chromosome 1 at 1p36[Fonatsch, et al., *Genomics* 14:825–6 (1992)]. CD30 is highly expressed in lymphoblastoid and H/RS cells and has been shown to promote a Th2 phenotype [Del Prete, et al., *J Exp Med* 182:1655–61 (1995)]. The possible roles of NF-IL-3 and Notch2, and their relationship to IL-13 and the CD30 antigen in the pathogenesis of HD lymphoma merit further investigation.

EXAMPLE 2

Northern Analysis and Cytokine Production

To evaluate the significance of the results from Example 1, Northern blots and ELISA were used to examine expression of IL-13, IL-5, GM-CSF, NF-IL-3, Notch2, and urokinase in the HD-derived EBV negative cell lines L428, KMH2, and HDLM2 [Drexler, *Leukemia and Lymphoma* 9:1–25 (1993)]. Control cell types included lymphoblastoid EBV-infected B cell lines LCL-GK and LCL-HO, and the three EBV-negative non-Hodgkin lymphoma (NHL)-derived cell lines with either B cell (Ly4, Ly7) or T cell (Ly13.2) phenotype.

In the Northern blot analysis, total RNA was isolated using Trizol reagent (Gibco BRL, Gaithersburg, Md.) according to the manufacturer's suggested protocol and 15 µg of total RNA was separated on a 1% formaldehyde agarose gel. Samples were run in 0.02 M MOPS (3-[N-morpholino]propanesulfonic acid), pH 7.0, 8 mM sodium acetate, and 1 mM EDTA The RNA was blotted overnight in 10×SSC onto a Hybond N+ nylon membrane (Amersham Pharmacia Biotec, Arlington Heights, Ill., USA) and crosslinked to the membrane using UV irradiation using standard techniques. Hybridization was carried out at 65° C. using α-[$^{32}$P] dATP-labeled oligonucleotides specific for the human Notch2, NF-IL-3, urokinase, IL-13, and human β-actin genes. Probe labeling was carried out using a Mutiprime DNA labeling system (Amersham Pharmacia Biotec, Arlington Heights, Ill., USA) according to the manufacturer's suggested protocol. Membranes were washed once at 65° C. for 30 minutes in 2×SSC containing 0.1% SDS, and then at 65° C. for 30 minutes in 0.2×SSC containing 0.1%SDS.

In the ELISA, cell culture supernatant ($10^5$ cells equivalent/ml) from each cell type was recovered 48 hours after medium exchange and assayed for IL-5, Il13, and GM-CSF production using Quantikine kits (R&D Systems, Minneapolis, Minn., USA) specific for each cytokine, according to the manufacturer's suggested protocol.

Results indicated that Notch2, urokinase, and NF-IL-3 were up-regulated in LCL or NHL cell lines, as well as in the HD-derived cell lines, but overexpression of IL-13, IL-5 and GM-CSF was restricted to the HD-derived cell lines. IL-5 and GM-CSF expression and secretion could be demonstrated only in L428 and KMH2 cells, but mRNA expression and secretion of IL-13 could be detected in all three HD-derived cell lines. HDLM2 cells secreted a moderate amount of IL-13 (27 pg/ml), while L428 and KMH2 cells secreted significantly higher levels of (4800 pg/ml and 6100 pg/ml, respectively).

EXAMPLE 3

In Situ Hybridization

To confirm that IL-13 was expressed by the rare H/RS tumor cells, in situ hybridization was carried out with sense and antisense RNA probes for IL-13 using lymph node biopsies from four untreated patients, newly diagnosed with classical nodular sclerosis HD. A benign reactive lymph node biopsy was used as a control.

For in situ hybridization, paraffin sections were mounted and fixed according to standard protocols. A human cDNA probe specific for IL-13 was generated by PCR using RT-PCR and IL-13-specific primers set out in SEQ ID NOs: 1 and 2. PCR was carried out using standard conditions well known and routinely practiced in the art.

5'GTTGACCACGGTCATTGCTCTCACT SEQ ID NO: 1

3'TTCAGTTGAACCGTCCCTCGCGAA SEQ ID NO: 2

The 388 bp amplification product was cloned into the pCRII vector (TA cloning kit, Invitrogen, Carlsbad, Calif., USA). Sense and antisense probes were synthesized from the linearized vector with SP6 or T7 polymerase, labeled with $^{32}$P-UTP, and processed as previously described [Hui, et al., *Nat Genet* 3:241–246 (1993)]. The sections were counterstained with toluidine blue using a standard protocol.

The results confirmed strong and specific IL-13 expression by morphologically identifiable H/RS cells in all patients, in contrast to background levels of IL-13 expression in non-H/RS cells and cells from the control biopsy.

EXAMPLE 4

Analysis of Cell Proliferation after Neutralization of IL-13

To investigate the effects of IL-13 and IL-5 on the proliferation of H/RS cells, L428, KMH2 and HDLM2 cells were incubated with either (i) medium alone, (ii) medium containing neutralizing antibodies to IL-13 or IL-5, or (ii) isotype matched control antibodies. Proliferation was measured by determining [$^3$H]-thymidine incorporation at 24, 48, or 72 hours after treatment.

HD-derived L428, KMH2, and HDLM2 cells and LCL control cells (2×10$^4$/well) were cultured in 96-well flat-bottom plates for 24 hours, 48 hours, or 72 hours in the presence of ant-IL-13, anti-IL-5, or isotype control antibodies at 5, 10, 20, 30, 50, 100 or 150 μg/ml. Cells were treated either with IL-13 (0.5, 1, 5, 10, 50, 100 and 200 ng/ml), or with these same doses of IL-13 combined with 20 μg/nl anti-IL-13 monoclonal antibody. Tritium- labeled thymidine (1 μCi/well) was added to each well and incubation continued for eight hours. Cells were harvested on filters and incorporation of [$^3$H]-thymidine into cellular DNA was measured as previously described [Shahinian, et al., *Science* 261:609–12 (1993)]. The viability of cultured cell lines after treatment with anti-IL-13 neutralizing antibodies was examined by 7-aminoactinomycin D (7-AAD) staining.

Results showed no significant differences in viability between HD-derived cells and controls. Neutralizing antibodies against IL-13 and IL-5 had no effect on the proliferation of control LCL-HO cells. After 72 hours treatment with 20 μg/ml anti-IL-13 neutralizing antibody, however, proliferation of HDLM2 cells (which secrete moderate levels of IL-13) was suppressed to 27% of that of untreated control cells. Treatment of L428 and KMH2 cells with up to 150 μg/ml anti-IL-13 antibody had no effect on the proliferation of the cell lines, perhaps because of their vigorous secretion of IL-13. No significant changes in proliferation were observed in control groups or HDLM2 cells treated with either isotype control antibodies or an anti-IL-5 neutralizing antibody. A combination of anti-IL-13 and anti-IL-5 antibodies did not inhibit proliferation to any greater extent than anti-IL-13 alone. Treatment with increasing concentrations of anti-IL-13 antibody demonstrated that the effect on the proliferation of HD-derived cells was dose-dependent. Furthermore, the anti-proliferative effect of anti-IL-13 on HDLM2 cells could be overcome by the addition of exogenous IL-13. Treatment of HDLM2 cells with exogenous IL-13 alone did not result in an increase in proliferation over that of untreated cells, suggesting that the cells produce saturating levels of IL-13 sufficient to support maximal proliferation.

Numerous modifications and variations in the invention as, set forth in the above illustrative examples are expected to occur to those skilled in the art. Consequently only such limitations as appear in the appended claims should be placed on the invention. References cited herein are incorporated by reference in their entireties.

---

---

What is claimed is:

1. A method for inhibiting Il-13 dependent proliferation of Hodgkin and Reed Sternberg Cell types comprising the step of contacting the H/RS cells with a compound that inhibits the biological activity of Il-13, wherein said biological activity is defined as the binding of Il-13 to the Il-13 receptor.

2. The method of claim 1 wherein the compound is an antibody.

3. The method of claim 2 wherein the antibody is selected from the group consisting of a human antibody, a humanized antibody, and a CDR-grafted antibody.

4. A method for inhibiting Il-13 dependent proliferation of Hodgkin and Reed Sternberg Cell types comprising the step of contacting the H/RS cells with a compound that inhibits the biological activity of Il-13 receptor expressed on the H/RS cell types, wherein said biological activity is defined as the binding of Il-13 to the Il-13 receptor.

5. The method of claim 4 wherein the compound is an antibody.

6. The method of claim 5 wherein the antibody is selected from the group consisting of a human antibody, a humanized antibody, and a CDR-grafted antibody.

7. A method for identifying a compound that inhibits IL-13 dependent proliferation of Hodgkin and Reed Sternberg (H/RS) cell types comprising the steps of a) measuring binding between IL-13 with IL-13 receptor in the presence and absence of a candidate inhibitor compound; and b) identifying the candidate compound as an inhibitor when binding between IL-13 and the IL-13 receptor is less in the presence of the candidate compound than in the absence of the candidate compound.

8. The method of claim 7 wherein the compound is an antibody.

9. The method of claim 8 wherein the antibody is selected from the group consisting of a human antibody, a humanized antibody, and a CDR-grafted antibody.

10. A method for identifying a compound that inhibits IL-13 dependent proliferation of Hodgkin and Reed Sternberg (H/RS) cell types comprising the steps of:
   a) contacting IL-13 with IL-13 receptor;
   b) measuring binding between IL-13 and the IL-13 receptor;
   c) repeating step (a) in the presence of a candidate inhibitor compound;
   d) repeating step (b) in the presence of the candidate compound; and
   e) identifying the candidate compound as an inhibitor when binding between IL-13 and the IL-13 receptor is less in the presence of the candidate compound than in the absence of the candidate compound.

11. The method according to claim 7 or 10 wherein the IL-13 receptor is expressed on the cell surface of the H/RS cell types.

12. A method for treating Hodgkin's Disease comprising the steps of administering to an individual in need thereof a therapeutically effective amount of a compound that inhibits IL-13 biological activity.

13. The method of claim 12 wherein the compound is an antibody.

14. The method of claim 13 wherein the antibody is selected from the group consisting of a human antibody, a humanized antibody, and a CDR-grafted antibody.

15. A method for treating Hodgkin's Disease comprising the step of administering to an individual in need thereof a therapeutically effective amount of a compound that inhibits IL-13 receptor biological activity.

16. The method of claim 15 wherein the compound is an antibody.

17. The method of claim 16 wherein the antibody is selected from the group consisting of a human antibody, a humanized antibody, and a CDR-grafted antibody.

* * * * *

SEQUENCE LISTING

<160> NUMBER OF SEQ ID NOS: 2

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 1
gttgaccacg gtcattgctc tcact                                         25

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 2
ttcagttgaa ccgtccctcg cgaa                                          24